(12) United States Patent
Gumbrecht et al.

(10) Patent No.: US 7,642,053 B2
(45) Date of Patent: Jan. 5, 2010

(54) METHOD AND DEVICE FOR PCR-AMPLIFICATION AND DETECTION OF NUCLEOTIDE SEQUENCES

(75) Inventors: Walter Gumbrecht, Herzogenaurach (DE); Manfred Stanzel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 224 days.

(21) Appl. No.: 10/539,437

(22) PCT Filed: Dec. 15, 2003

(86) PCT No.: PCT/DE03/04136

§ 371 (c)(1), (2), (4) Date: Mar. 20, 2006

(87) PCT Pub. No.: WO2004/057022

PCT Pub. Date: Jul. 8, 2004

(65) Prior Publication Data

US 2006/0234236 A1  Oct. 19, 2006

(30) Foreign Application Priority Data

Dec. 19, 2002  (DE) ............................ 102 59 819

(51) Int. Cl.
*C12Q 1/68*  (2006.01)
*C12P 19/34*  (2006.01)
(52) U.S. Cl. .................................. 435/6; 435/91.2
(58) Field of Classification Search ............... None
See application file for complete search history.

(56) References Cited

U.S. PATENT DOCUMENTS

| | | | |
|---|---|---|---|
| 5,736,257 A | | 4/1998 | Conrad et al. |
| 6,258,606 B1 | | 7/2001 | Kovacs |
| 2002/0115293 A1 | * | 8/2002 | Ghodsian .................... 438/689 |
| 2002/0155586 A1 | * | 10/2002 | Cheng et al. ............. 435/287.1 |
| 2004/0048270 A1 | | 3/2004 | Zeltz et al. |
| 2004/0101442 A1 | * | 5/2004 | Frechet et al. ................ 422/99 |

FOREIGN PATENT DOCUMENTS

| | | |
|---|---|---|
| DE | 196 10 115 G2 | 9/1997 |
| JP | 2001-525921 | 11/2001 |
| WO | WO 98/01758 | 1/1998 |
| WO | WO 99/36576 A1 | 7/1999 |
| WO | WO 00/58522 A | 10/2000 |
| WO | WO 00/60919 A | 10/2000 |
| WO | WO 00/62036 A | 10/2000 |
| WO | WO 01/34842 A2 | 5/2001 |
| WO | WO 01/42508 A2 | 6/2001 |
| WO | WO 02/20833 A2 | 3/2002 |

OTHER PUBLICATIONS

Fuchs et al: "A silicon lab-on-chip for integrated sample preparation by pcr and dna analysis by hybridization" Annual International IEEE-EMBS special topic conference on microtechnologies in medicine and biology. Proceedings. XX, XX, May 2, 2002, S. 227-231, XP001180969.

Hodko O et al: "Detection of pathogens using on-chip electrochemical analysis of pcr amplified dna molecules", Proceedings of the Spie, Spie, Bellingham, VA, US, Bd. 4265, Jan. 25, 2001. S. 65-74, XP008000573.

Sosnowski R G et al: "Rapid determination of single base mismatch mutations in dna hybrids by direct electric field control" Proceedings of the national academy of sciences of USA, National Academy of Science, Washington, US, Bd. 94, Feb. 1997, S. 1119-1123, XP000857636.

Gilles P N et al: "Single nucleotide poymorphic discrimination by an electronic dot blot assay on semiconductor microchips" Nature Biotechnology, Nature Publishing, US, Bd. 17, Apr. 1999, S. 365-370.

Tillib SV, Strizhkov BN, Mirzabekov AD, Datenbank PubMed bei NCBI, Anal. Biochem. (2001) 292 (1) 155-60.

Dubiley, S. U.A.: Polymorphism analysis and gene detection by minisequencing on an array of gel-immobilized primers, Nucleic Acids Research, 1999, vol. 27, No. 18, e19, 1-6.

Strizhkov, B.N. u.a.: PCR amplification on a microarray of gel-immobilized oligonucleotides: detection of bacterial toxin- and drug-resistant genes and their mutations. Biotechniques (2000) 29 (4) 844-8, 850-2, 854.

Koichinski. A. & Mirzabekov A.: Analysis of SNPs and other genomic variations using gel-based chips, Hum Mutat. (Apr. 2002) 19 (4) 343-60.

Fuchs et al: "A silicon lab-on-chip for Integrated sample preparation by PCR and DNA analysis by hybridization", Annual International IEEE-EMBS Special Topic Conference on Microtechnologies in Medicine and Biology. Proceedings, May 2, 2002, S. 227-231.

European Patent Office Action dated Apr. 24, 2008 for corresponding European Patent Application No. 03 785 579.8.

\* cited by examiner

*Primary Examiner*—Kenneth R. Horlick
*Assistant Examiner*—David C Thomas
(74) *Attorney, Agent, or Firm*—Harness, Dickey & Pierce, P.L.C.

(57) ABSTRACT

A DNA-Chip includes a flat carrier and an array of spots containing probe molecules (oligonucleotides) which are arranged on said carrier. Each spot is associated with a microelectrode arrangement for impedance spectroscopic detection of binding events occurring between the probe molecules and target molecules (DNA fragments) applied by way of an analyte solution. In order to increase the sensitivity or the binding specific measuring effects of the biochip, the electrode arrangement is at least partially embedded in a hydrophilic reaction layer containing probe molecules and which is permeable to target molecules.

13 Claims, 6 Drawing Sheets

METHOD AND DEVICE FOR PCR-AMPLIFICATION AND DETECTION OF NUCLEOTIDE SEQUENCES

This application is a PCT National Stage Application of PCT/DE2003/004136 filed Dec. 15, 2003, which claims priority under on German Patent Application No. DE 102 59 819.3 filed in Germany on Dec. 19, 2002, the entire contents of which is hereby incorporated herein by reference.

FIELD

The invention generally relates to a method for PCR amplification and detection of nucleotide sequences. A method of this kind serves, for example in medical diagnostics, to track down infectious target sequences of viral or bacterial DNA. In addition, the invention also generally relates to a corresponding device for carrying out the method.

BACKGROUND

During a PCR (Polymerase Chain Reaction), the sample to be investigated is subjected to a cyclical temperature treatment in which the DNA fragments are essentially duplicated with the aid of a primer pair and a polymerase. For this kind of analyses, there are nowadays processes available in which the PCR is carried out on a microchip which has an array of microspots which form "gel pads" (WO 01/34842 A2). In order to enable hybridizations within the microspots to be detected by fluorescence spectroscopy, the known processes involve adding a labeled primer to the analyte solution.

Methods for amplifying and detecting nucleic acids are known from the prior art. Here, gel pads may form separate microspots as hydrophilic reaction layers on a microarray, said gel pads containing oligonucleotides which can hybridize with target nucleic acids to be identified. Furthermore, the printed publication "Nucleic Acids Res." (1999) 27 (18) e19, pages 1 to 6, discloses carrying out amplification reactions in gel pads on a microarray and detection reactions by way of single base elongation. In this connection, mention should further be made of DE 196 10 115 C2 which discloses an array having a microelectrode arrangement and of WO 01/42508 A2 which discloses gel pads with immobilized probes in contact with microelectrodes.

Finally, WO 99/36576 A1 involves the use of gel pads in an array and also methods and systems for their preparation, it being intended to prepare "intelligent gels" as reaction layers.

SUMMARY

It is an object of an embodiment of the invention to propose an improved method for amplification and detection of nucleotide sequences, which makes possible continuous monitoring of the PCR and, in particular, simultaneous investigation of a plurality of target sequences or a plurality of mutations of a target sequence in a simple manner. In addition, it is intended to produce a device which makes possible, in particular, an electrochemical measurement.

The method of an embodiment of the invention includes the following:

a) providing a microchip having an array of a plurality of microspots forming analytical positions, which in each case comprise a hydrophilic reaction layer and a microelectrode arrangement embedded therein, said reaction layer comprising as probe molecule at least one immobilized oligonucleotide which is hybridizable with a target sequence to be identified of a DNA fragment, b) applying an analyte solution comprising a plurality of target sequences and PCR reagents to the microchip in such a way that it completely covers the array, c) subjecting the array to a thermocycling process in order to amplify the target sequences, d) detecting hybridization events on probe molecules immobilized at one analytical position with the aid of the microelectrode arrangement assigned to said position.

This method of at least one embodiment has first of all the advantage that it is possible to detect binding or hybridization events in a microspot from the start of the PCR, without interruption of the ongoing reaction cycles and with minimum equipment. Since the microspots contain electrode arrangements which are independent of one another, each analytical position can be addressed individually and thus correlated to a particular probe molecule or a desired target sequence.

It is therefore possible to monitor a hybridization in a multiplicity of microspots in a very simple manner at the same time. In contrast, optical read out would require an optical recording system which is technically complex, if only due to the small size of the spots and their arrangement in a very narrow space. The technical complexity becomes even greater, if arrays having a large number of microspots are to be read out.

Owing to their electric partial charges, the nucleotide sequences held in a microspot by hybridization with immobilized probe molecules alter electrical parameters such as, for example, the conductance within a microspot or the impedance of an electrode arrangement. This makes possible an electrochemical or electrical evaluation using a device of an embodiment of the invention including a biochip with microelectrode arrangement.

DE 196 10 115 C2 discloses a biochip which can be read out impedance-spectroscopically and which already contains a plurality of interdigital electrode arrangements on a carrier, with probe molecules being immobilized on the electrodes and on the surfaces located between said electrodes. However, this kind of detecting binding events has the problem that the dimensions of the electrode structures differ from molecular dimensions by orders of magnitude.

It is possible, with still justifiable technical complexity, to prepare electrodes which have a width of between 1 and 10 µm, in particular of about 5-10 µm, are at a distance of the same size and have a thickness of from about 0.1 to 0.5 µm. The impedance-spectroscopically recordable range of the electric field of such an electrode arrangement extends from about 5 to 10 µm beyond the carrier surface or the plane formed by the electrode arrangement. In contrast, a probe molecule having, for example, 100 base pairs has a length of only about 30 nm, i.e. 0.3 µm. The influence of binding events in a monomolecular layer of probe molecules, immobilized on the sensor area or the electrodes, on the electric field or on the impedance of the electrode arrangement is correspondingly low.

Due to the fact that, according to an embodiment of the invention, the electrode arrangement is embedded at least partially in a hydrophilic reaction layer containing probe molecules and permeable for target molecules, it is possible to collect within the reaction layer a much higher number of probe molecules or target sequences than in a monomolecular layer. This results in a much larger influence of the electric field or of the impedance-spectroscopic recording range of the electrode arrangement.

A biochip designed in this way has a correspondingly higher measuring sensitivity. In contrast, in the case of conventional biochips, an increase in the concentration of the target sequences, obtained by PCR, would not result in an increase in sensitivity, owing to the small supply of probe molecules.

The reaction layer used in the method of an embodiment of the invention must be thermally stable to about 95° C. in order to carry out a PCR. Thermally stable here means that the composition of the reaction layer is even at the temperature indicated such that it holds onto probe molecules, that hybridization/denaturation (melting) of target sequences and probe molecules can take place in it unimpededly and that it also essentially retains its other properties. For immobilization, the reaction layer preferably contains polymers with coupling groups to which probe molecules are covalently bound. This guarantees for sure that binding pairs of target sequences and probe molecules are retained in the reaction layer during rinsing processes following a PCR.

A particularly suitable reaction layer includes or even consists of a hydrogel. Hydrogels form an aqueous environment in a mechanically stable form, which permits mass transfer with a predominantly aqueous analyte. Free-radically crosslinkable hydrogels based on acrylamide, with maleic anhydride and/or glycidyl (meth)acrylate as coupling groups, have proved particularly suitable.

In a further preferred embodiment, the flat carrier of the biochip includes silicon (Si) as substrate and an insulating layer connected therewith, the side of the latter, which faces away from the silicon layer, carrying the electrode arrangement and the reaction layer. Such an arrangement enables the electrical interconnection of the electrode arrangement to be implemented using the technology known from Si memory chips.

A particular advantage of the proposed method is the fact that the method permits a larger variety of different possible designs in the case of simultaneous or multiplex studies. The reason for this is, inter alia, that it is not necessary to incorporate a label into amplicons produced during the PCR, which, especially in complex tests, holds the risk of undesired interactions arising between the substances required for labeling and between these and target sequences to be identified.

BRIEF DESCRIPTION OF THE DRAWINGS

Further details and advantages of the invention are obtained from the description of the figures below of example embodiments on the basis of the drawings. In the figures.

DETAILED DESCRIPTION OF THE EXAMPLE EMBODIMENTS

Figure 1:
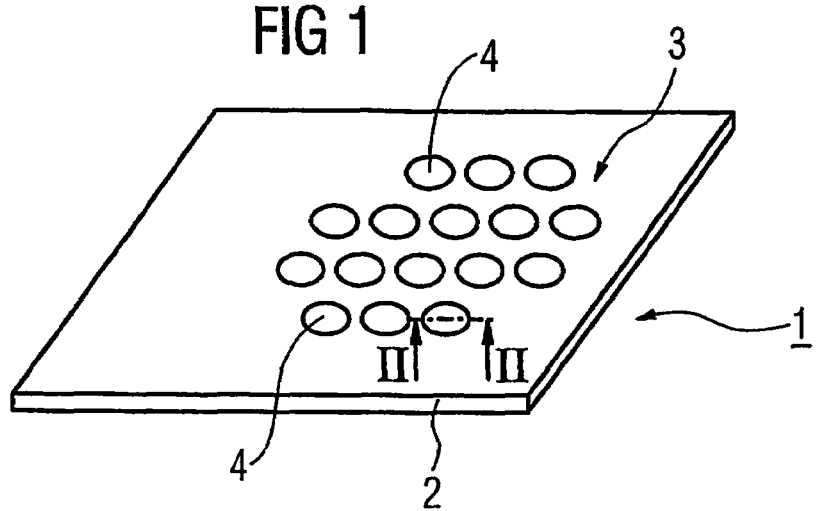
FIG. 1 depicts a simplified perspective representation of a microchip comprising a flat carrier and an array of microspots.

As FIG. 1 indicates, an element referred to as biochip 1 includes a flat carrier 2 to one side of which a spot array 3 has been applied. A microspot referred to hereinbelow as spot 4 contains immobilized probe molecules, for example oligonucleotides. If an analyte solution containing unknown target molecules is applied to a spot 4, then the target molecule couples to the probe molecule, if the base sequences correspond to one another. The property change caused by such a binding event, for example changes in the specific resistance, the impedance or the dielectricity constant, can be recorded by an electrode arrangement 5.

Figure 2:
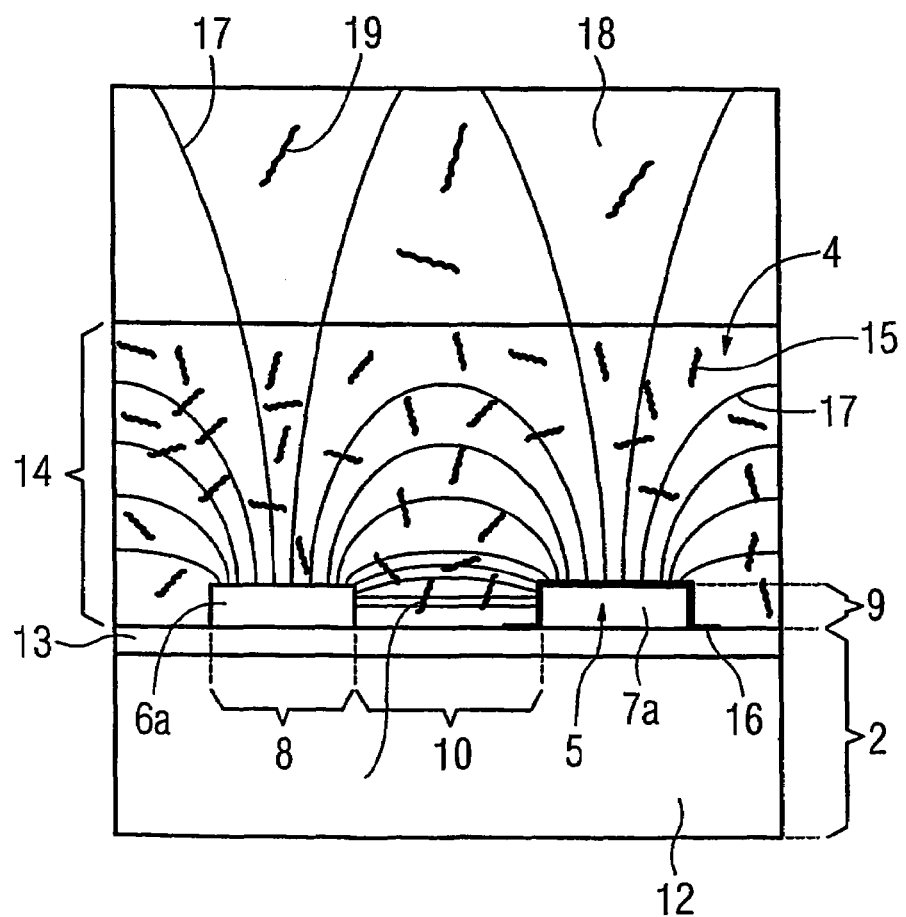
FIG. 2 depicts a cross section through a spot according to line II-II in FIG. 1, as an enlarged detail.
Figure 3:
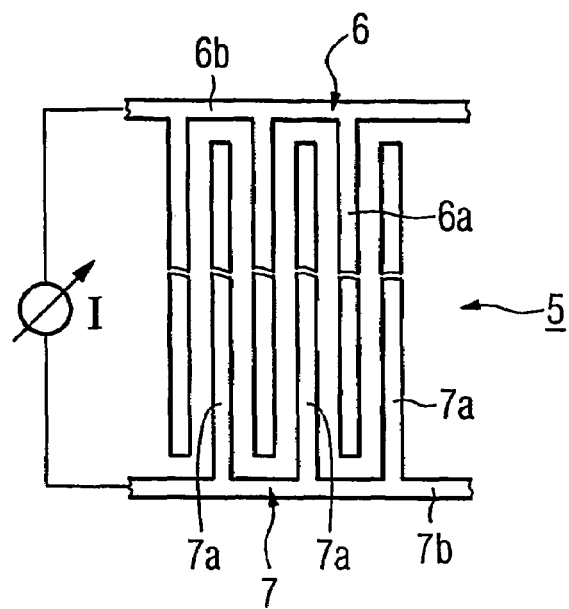
FIG. 3 depicts a detail of an electrode arrangement assigned to a spot.
Figure 4:
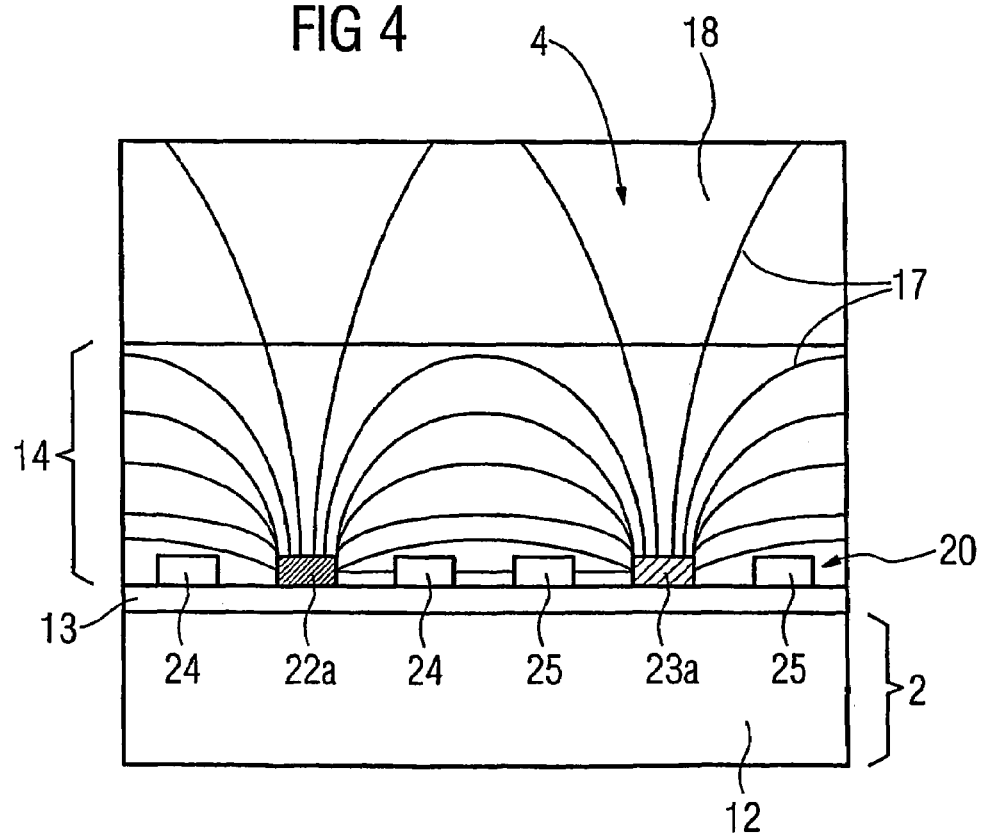
FIG. 4 depicts an embodiment of a microchip having a 4-pole electrode arrangement in a representation corresponding to FIG. 2.
Figure 5:
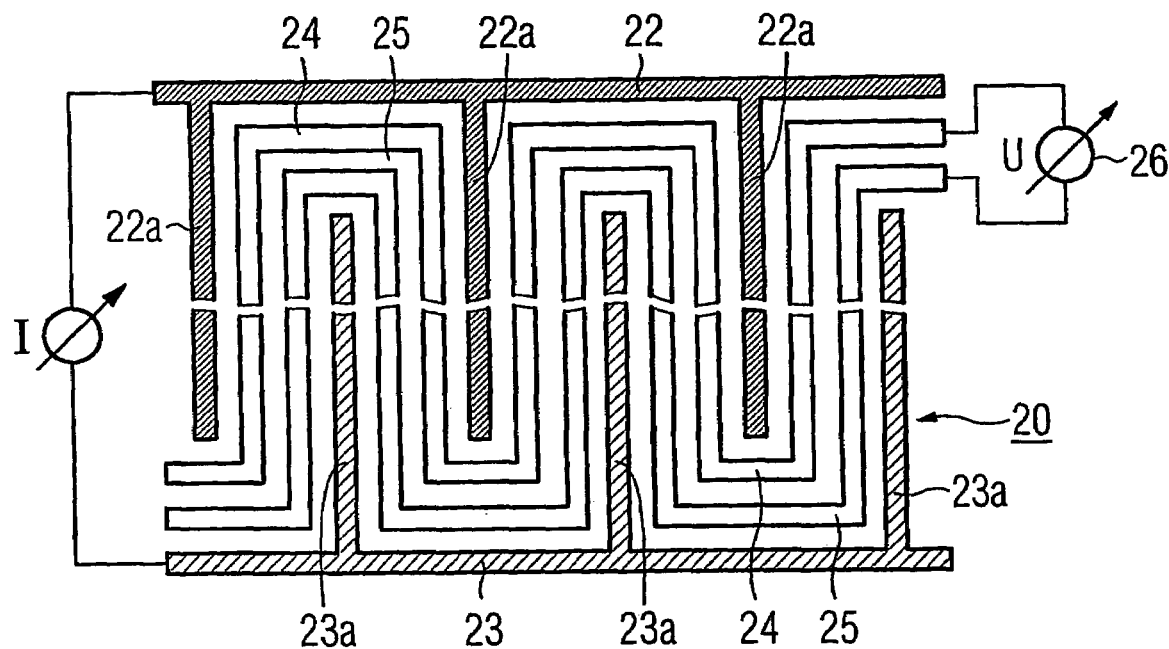
FIG. 5 depicts the electrode arrangement of the microchip of FIG. 4 in a representation corresponding to FIG. 3.

The spot array 3 or microchip 1 with electrodes implemented therein forms a device which permits online monitoring. Such a device may have different electrode arrangements which are depicted in FIGS. 3 and 5. FIGS. 2 and 4, in contrast, depict the phenomenology of immobilization and measurement in such arrangements.

The example embodiment of FIG. 2 contains a two-pole electrode arrangement. The latter has been applied, for example, with the aid of a photolithographic process on the flat carrier 2. The electrode arrangement 5 includes two electrodes 6, 7 which have the form of an interdigital structure, i.e. each electrode includes a plurality of strip-like partial electrodes 6a, 7a parallel to one another, which extend in each case into the space between two partial electrodes of the in each case other electrode. The partial electrodes 6a, 7a are connected to one another by a likewise strip-like connecting conductor 6b, 7b which extends at an angle to the partial electrodes 6a, 7a.

A high-frequency alternating current in the megahertz range is applied to the electrodes 6, 7. The width 8 of the partial electrodes 6a, 7a is approx. 1 µm, their height 9 is from about 100 to 500 nm. The distance 10 between the partial electrodes 6a, 7a is likewise approx. 1 µm.

The flat carrier 2 includes a silicon layer 12 and an insulating layer 13, including or even consisting of a polymer and arranged between said silicon layer and the electrodes 6, 7. The electrical interconnections and parts required, for example for an impedance-spectroscopic measurement of binding events, are implemented in the usual way by way of an appropriate topology of the silicon layer, and this is not shown in FIG. 2 in any detail.

A reaction layer 14 composed of a hydrogel which will be described in more detail below has been applied to the insulating layer 13. It may be expedient to provide the flat carrier 2 or the silicon layer 13 in the region of a spot with a depression filled with the reaction layer 14 (see FIGS. 6, 8-10). Probe molecules 15 are embedded and homogeneously distributed in the reaction layer 14 or the hydrogel, and this is depicted in FIG. 2 in an enlarged and symbolic manner. A probe molecule of 300 bases has a length of about 100 nm. Consequently, a unimolecular layer of probe molecules in conventional microchips has a thickness which at most corresponds about to the line 16 in FIG. 2.

It is readily understood that such a layer can take relatively few probe molecules 15 and, correspondingly, can influence the electric field of the electrode arrangement only slightly in the case of binding or hybridization events. In contrast to this, the reaction area in a microchip of the invention, which area contains probe molecules 15 and is penetrated by field lines 17, is substantially enlarged and offers space for a several powers of ten higher number of probe molecules 15. If an analyte solution 18 is applied to a spot array 3 designed in this way or to a spot 4, then the target molecules 19 or target sequences contained therein and depicted in FIG. 2 likewise on an exaggerated scale and only symbolically find a substantially larger number of possible binding partners in the form of the probe molecules 15.

The dimensions of the reaction layer 14 and its thickness, for example from 5 to 10 μm, are preferably such that the impedance-spectroscopic recording range is basically completely utilized, this being the case at a thickness of the reaction layer of from about 5 to 10 μm. It is thus possible, at an appropriate concentration of probe molecules 15 in this range, to increase the binding-specific measurement effect of the microchip substantially. The composition of the reaction layer is such that it provides an aqueous reaction medium. It is furthermore such that target molecules 19 or else other substances required for a reaction, for example polymerase, can diffuse into said layer, without their reactivity being impaired in the process.

As already mentioned above, the reaction layer 14 used according to an embodiment of the invention is a hydrogel. A hydrogel is an aqueous environment in a mechanically stable form with simultaneous guarantee of mass transfer in a predominantly aqueous surrounding. It is possible, by choosing the chemical composition, with respect to the components and the ratios between them, to vary the properties of the hydrogels, such as water content, swelling behavior, mechanical stability, etc., over a wide range.

A hydrogel, which can be easily prepared and which has good adhesion both to the electrode arrangement 5 and to the insulating layer 13, is a free-radically crosslinkable hydrogel based on acrylamide, which contains a comonomer which enables correspondingly modified probe molecules to be covalently coupled via linker groups. The hydrogel includes, in addition to the monomeric precursor of the polyacrylamide, a crosslinker, at least one free radical initiator, at least one comonomer with reactive linker groups and, where appropriate, at least one plasticizer.

After preparing the layer and subsequent thermal or photocrosslinking, a water-swellable hydrogel is obtained which contains reactive linker groups for the immobilization of probe molecules. Crosslinkers which are employed are methylenebisacrylamide and/or dimethylacrylic esters, for example tetraethylene glycol dimethacrylate.

The mesh size of the hydrogel can be adjusted by varying the concentrations of the crosslinker. The comonomer used contains maleic anhydride and/or glycidyl (meth)acrylate. Suitable plasticizers are mono-, di- and/or triethylene glycol. The reactants mentioned are mixed with a polar, water-miscible solvent, preferably with dimethylformamide. The processing viscosity can be adjusted by varying the proportion of the solvent. Adhesion to the surface of the flat carrier and to the electrode arrangement 5 can be enhanced by adding customary adhesion promoters, for example based on silane.

FIGS. 4 and 5 depict a four-pole electrode arrangement 20. The electrode arrangement 20 is composed of two current electrodes 22, 23 and two voltage or probe electrodes 24, 25. The current electrodes 22, 23 are arranged and designed according to the electrode arrangement 5 of the exemplary embodiment of FIG. 2. The probe electrodes 24, 25 are likewise strip-like and extend in the form of a meandering double strand through the spaces between the partial electrodes 22a and 23a.

A high-frequency alternating current is applied to the current electrodes 22, 23. A voltage meter 26 which enables a change in the electric alternating field as a result of hybridization events to be detected is connected to the probe electrodes 24, 25. The measurement can thus be carried out independently of the current electrodes so that, for example, the polarization of the latter, which increases the capacitance of the electrodes, cannot affect the measurement.

In contrast, in the case of a two-pole electrode arrangement, electrode capacitance has to be kept low by use of a correspondingly high measuring frequency unsuitable for the measurement. This is done in order to be able to determine the resistance of the analyte solution or of the reaction layer, which is decisive for the measurement.

Figure 6:
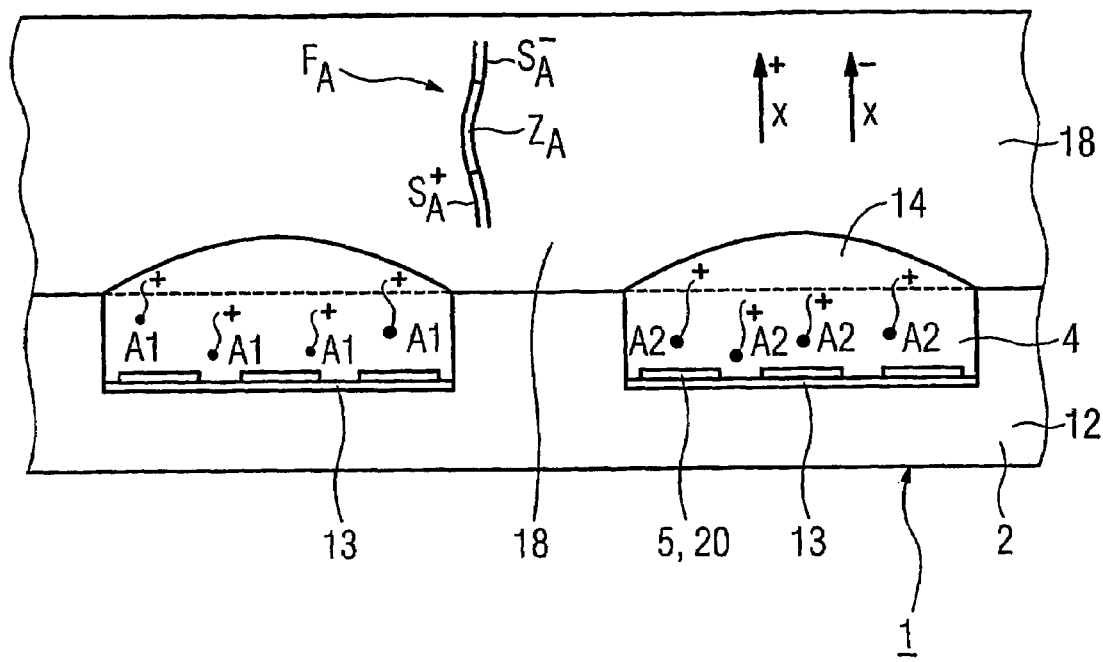
FIG. 6 depicts a diagrammatic representation which illustrates a first method variant of a PCR-assisted analysis.

In a variant of the method, depicted diagrammatically in FIG. 6 (for this and for FIGS. 8 to 10, see the figure legend indicated further below), an analysis solution 18 which contains a DNA fragment $F_A$ with a target sequence $Z_A$, an external primer pair and the reagents required for a PCR, such as a Taq (DNA) polymerase, dNTPs (deoxynucleoside triphosphate) etc., is applied to a microchip 1. The target sequence $Z_A$ is one which can occur in a plurality of different variants, for example typing of viruses, e.g. HIV or HPV.

Each possible variant ($Z_{A1}$, $Z_{A2}$, etc.) has at least one separate spot 4A1, 4A2 etc. assigned to it, with a single oligonucleotide type which can hybridize with a specific target sequence being immobilized as probe molecule within the reaction layer 14 of the particular spot. Amplification (PCR) of the target sequence $Z_A$, which is carried out in the usual way using a thermocycling process, takes place only in the mobile phase 18.

Figure 7:
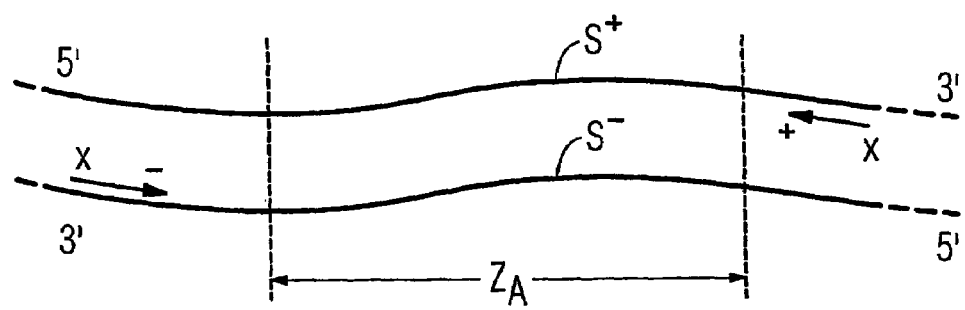
FIG. 7 depicts a diagrammatic drawing which indicates the mode of action of an unspecific primer pair.

Preference is given to using a primer pair which couples (hybridizes) outside the target sequence $Z_A$, as indicated in FIG. 7. The copied double strand, i.e. strand $S^+$ and counter-strand $S^-$, detach from one another during denaturation (melting). Normally, the strand $S^+$ (sense strand) is used for identifying a target sequence. Accordingly, oligonucleotides which hybridize exactly with this strand are immobilized in the spots 4A1, 4A2. In the simplest case of the presence of only one DNA fragment $Z_{A1}$, the amplified target sequence $Z_{A1}$ accumulates due to hybridization in that spot in which the correspondingly complementary capture oligonucleotide $Z_{A1}$ is immobilized.

Figure 8:
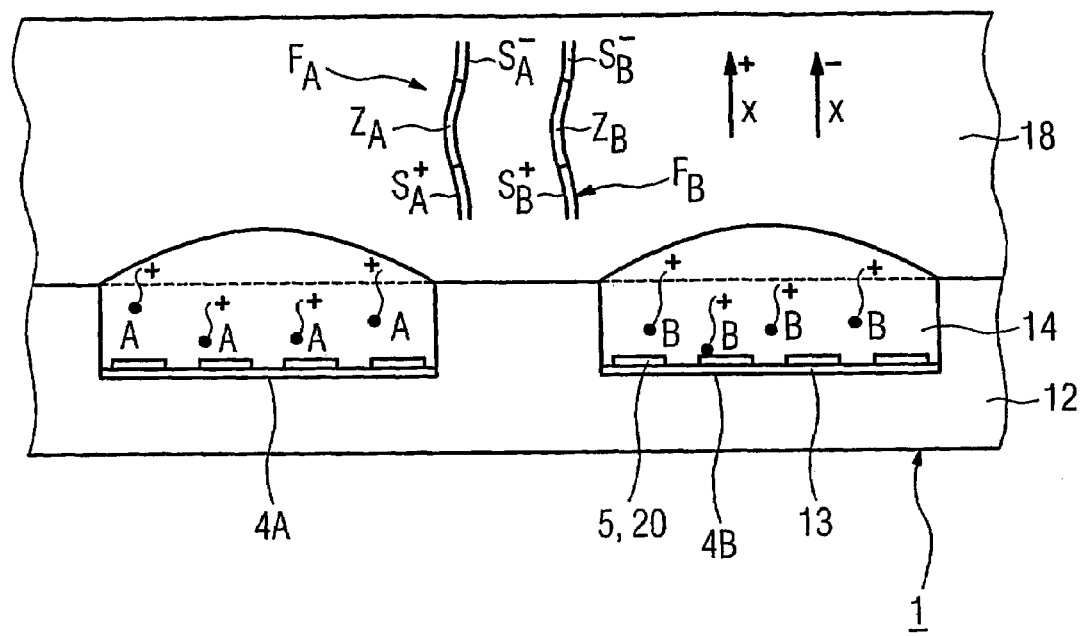
FIG. 8 depicts a diagrammatic representation of a modification of the first method variant.

In the method variant indicated in FIG. 8, the analyte solution 18 contains various types of DNA fragments. Two of those DNA fragments, $F_A$ and $F_B$, are shown by way of example. One or all of the DNA fragment/s present in the analyte solution 18 may be those according to the method variant of FIG. 6.

In this case, different groups of spots are to be provided, with typing of the variants of one DNA fragment being assigned to each group. However, the analytical investigation may also aim at "completely" different DNA fragments. In this case, it is sufficient in principle to assign in each case a single analysis spot 4A, 4B to a DNA fragment $F_A$, $F_B$. As in the method variant of FIG. 6 too, the analyte solution 18 here contains an external primer pair. The latter is selected so as to be suitable for the amplification of all DNA fragments $F_A$, $F_B$ to be analyzed (multiplex PCR).

The capture oligonucleotides indicated in FIG. 6 and FIG. 8 may act as primers in further method variants, if they can be extended by DNA polymerases. If the reaction layer 18 is permeable for DNA polymerase and the template/s and the further components of the PCR reaction, elongation of the immobilized oligonucleotides takes place according to the sequence of the hybridized matrix.

Figure 9:
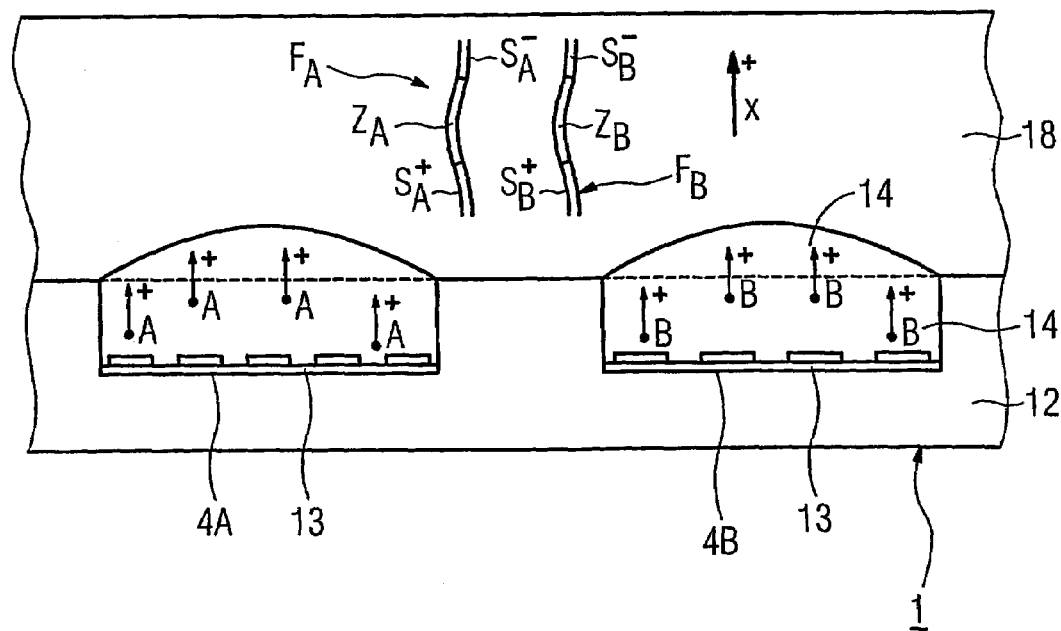
FIG. 9 depicts a diagrammatic representation of a second method variant.

In the method variant indicated in FIG. 9, a plurality of different DNA fragments according to the method variants of FIG. 6 or of FIG. 8 are present. Two of such DNA fragments, $F_A$ and $F_B$, are shown by way of example.

While in the method variants described above a primer pair was added to the analyte solution, now the solution contains only one primer of said primer pair in a mobile and dissolved form. This primer is unspecific, i.e. it is an external primer which couples to all DNA fragments $F_A$ and $F_B$ present in the analyte solution outside the target sequence $Z_A$ and $Z_B$ to be detected (preferably to the sense strand).

After denaturing of the analyte solution, the DNA single strands diffuse arbitrarily into the spots. Specific oligonucleotide capture molecules which bind directly upstream of the target sequence of the analyte DNA are immobilized in these spots. A hybridization takes place only where the analyte DNA hits complementary immobilized oligonucleotides (capture molecules).

In the subsequent elongation step of the PCR, the 5' end of the capture oligonucleotides which have previously captured (bound) selectively the DNA fragments to be detected is extended according to the information of the hybridized template. The capture molecule thus becomes the primer for the DNA polymerase reaction. The latter indicates that elongation can occur only in a microspot which also contains the capture molecule complementary to the target sequence.

In the case of the diagram in FIG. 9, strand $S^+$ of the DNA fragment $F_A$ in spot 4A and strand $S^+$ of the DNA fragment $F_B$ in spot 4B are copied by way of elongation of the particular immobilized primer/capture molecule. In the reannealing reaction following the particular amplification step and the melting, the target sequences which were originally present and those which have been produced in the solution anew accumulate on complementary capture molecules or sequences.

Owing to the increase in the concentration of the target sequence due to the preceding PCR cycle, these sequences will also bind to capture oligonucleotides which have not yet been extended and are present in their original form. Thus, the next PCR elongation step will start from these primers which have been produced de novo by the hybridization. This results in an increase in the concentration of extended capture molecules with each PCR cycle. This increase in the concentration of capture molecules/primer extended by about 100-300 bases (compared to 20-30 bases originally) causes a change in the electrical field or resistance, which may be measured with the aid of the electrode arrangement 5 or 20 and utilized for PCR monitoring (on-line PCR).

Figure 10:
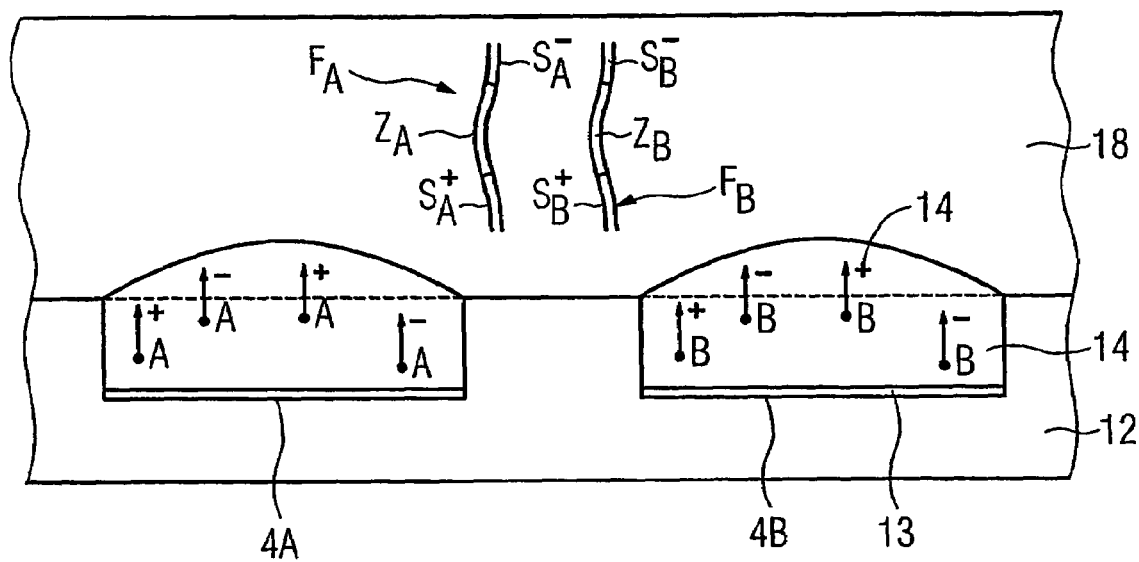
FIG. 10 depicts a diagrammatic representation of a third method variant.

In the method variant of FIG. 10, the analyte solution 18 contains one or more DNA fragment species according to the method variants of FIG. 6 or FIG. 8. While in the variants of FIG. 6 and FIG. 8 primer pairs and in the variant of FIG. 9 only one primer of the primer pair/primer pairs were added to the analyte solution, the solution here does not contain any dissolved free primers. The elongation reactions here take place in the individual microspots 4A, 4B, etc.

In contrast to all other method variants, here (FIG. 10) both capture molecules of the capture molecule pair which are needed for the specific detection of the two DNA strands of the target sequence are immobilized in each case in the same gel spot, i.e. an immobilized internal capture molecule/primer pair which hybridizes to a target sequence is present. After melting (denaturing) of the sample, the DNA single strands diffuse randomly into the spots. The strand $S_A^+$ or $S_A^-$ hybridizes with its 5' or 3' end to the complementary primer of the primer pair in spot 4A.

According to FIG. 10, the $S^+$ strand of the DNA fragment $F_A$ binds to a primer indicated by $A^+$ and the $S^-$ strand of the DNA fragment $F_A$ binds to a primer indicated by $A^-$, in each case at spot 4A. Subsequently, an antiparallel strand $S^-$ or $S^+$ is formed which is then likewise immobilized, since it has been synthesized by way of elongation of the immobilized primer $A^+$ or $A^-$.

In contrast to this, the 3' end of the elongated strand $S^-$ or $S^+$ moves freely and can hybridize with a counterprimer $A^-$ or $A^+$ immobilized in its proximity in the reaction layer. From this, the following amplification step results in an $S^+$ or $S^-$ strand which is likewise immobilized since it was formed by way of elongation of the immobilized primer $A^+$ or $A^-$.

The increase in the concentration of appropriately extended capture molecules, which occurs in each PCR cycle, causes, as has been described already further above, a change in the electric field or resistance. This may be utilized with the aid of the electrode arrangement 5 or 20 for PCR monitoring, thus making online PCR possible.

The novel method for amplification and detection of nucleotide sequences, which has been described in detail above, uses a biochip as described in the alternatives as a two-pole or four-pole arrangement in FIGS. 2 and 4.

It is apparent, especially from FIGS. 2 and 4, that the biochip suitable for the method described, including the reaction layer arranged thereupon and the analyte solution in contact therewith, is arranged in a housing depicted as a frame in said figures. According to FIGS. 6 and also 8 to 10, the housing is open at the side so that the analyte solution can flow through past the reaction layer.

Legend of the symbols in the above description and the figures:

↑=primer, in solution x=unspecific

A,B=relating to a particular DNA fragment

⊥=immobilized oligonucleotide, without primer function

□=immobilized primer

F=DNA fragment

S=single strand of a DNA fragment

+/−=relating to a coding/noncoding strand

Example embodiments of the present invention being thus described, it will be obvious that the same may be varied in many ways. Such variations are not to be regarded as a departure from the spirit and scope of the present invention, and all such modifications are intended to be included within the scope of the present invention.

What is claimed is:

1. A method for PCR amplification and detection of nucleotide sequences, comprising:
   using a hydrophilic reaction layer having coupling groups for covalent binding of probe molecules and an array of a plurality of microspots forming analytical positions, said microspots including, as probe molecules, at least one immobilized oligonucleotide which is hybridizable with a target sequence to be identified of a DNA fragment;
   applying an analyte solution including PCR reagents and a plurality of target sequences to the microspots such that the analyte solution completely covers the array;
   subjecting the array to a thermocycling process to amplify the target sequences; and
   detecting hybridization events on the probe molecules immobilized at one of the analytical positions electrochemically with the aid of a microelectrode arrangement wherein detected nucleotide sequences alter impedance of the microelectrode arrangement and a label is excluded from the detected nucleotide sequences.

2. The method as claimed in claim 1, wherein the reaction layer used is a hydrogel.

3. The method as claimed in claim 1, wherein a free-radically crosslinkable hydrogel based on at least one of acrylamide with maleic anhydride and glycidyl (meth)acrylate as coupling groups is used.

4. The method as claimed in claim 1, wherein a biochip including a semiconductor layer and an insulating layer connected therewith is used, wherein the electrode arrangement and the reaction layer are carried on a side of the insulating layer, which faces away from the semiconductor layer.

5. The method as claimed in claim 4, wherein the semiconductor layer used is a silicon layer.

6. The method as claimed in claim 1, wherein the analyte solution includes an external primer pair.

7. The method as claimed in claim 1, wherein the analyte solution includes a plurality of DNA fragments having a different target sequence and a single external primer pair suitable for the amplification of all of the target sequences.

8. The method as claimed in claim 1, wherein subjecting the array to the thermocycling process includes elongating a counter strand within the reaction layer with the aid of an internal primer immobilized in the reaction layer, wherein the analyte solution includes an external primer acting together with one strand of the DNA fragment.

9. The method as claimed in claim 1, wherein the analyte solution includes an internal primer pair which specifically hybridizes with one of the target sequences, the internal primer pair being immobilized in one of the microspots.

10. The method as claimed in claim 1, wherein the analyte solution includes a primer pair which hybridizes with a target DNA outside of the target sequences.

11. The method as claimed in claim 1, wherein subjecting the array to the thermocycling process includes elongating a counter strand of the DNA fragment within the reaction layer with the aid of a primer which specifically hybridizes with one of the target sequences in the analyte solution, the analyte solution including an external primer acting together with one strand of the DNA fragment.

12. The method as claimed in claim 1, wherein each electrode of the microelectrode arrangement has a width of 1-μm to 10-μm and a height of 100-nm to 500-nm.

13. The method as claimed in claim 1, wherein the reaction layer has a thickness of 5-μm to 10-μm.

* * * * *